(12) United States Patent
Zheng

(10) Patent No.: US 10,799,214 B2
(45) Date of Patent: Oct. 13, 2020

(54) ULTRASONIC SENSING DEVICE

(71) Applicants: Interface Technology (ChengDu) Co., Ltd., Chengdu (CN); INTERFACE OPTOELECTRONICS (SHENZHEN) CO., LTD., Shenzhen (CN)

(72) Inventor: Xiao-Bing Zheng, Shenzhen (CN)

(73) Assignees: Interface Technology (ChengDu) Co., Ltd., Chengdu (CN); INTERFACE OPTOELECTRONICS (SHENZHEN) CO., LTD., Shenzhen (CN)

( * ) Notice: Subject to any disclaimer, the term of this patent is extended or adjusted under 35 U.S.C. 154(b) by 691 days.

(21) Appl. No.: 15/666,825

(22) Filed: Aug. 2, 2017

(65) Prior Publication Data

US 2018/0263601 A1    Sep. 20, 2018

(30) Foreign Application Priority Data

Mar. 15, 2017 (CN) .......................... 2017 1 0152395

(51) Int. Cl.
*A61B 8/00* (2006.01)
*A61B 8/08* (2006.01)
*B06B 1/06* (2006.01)

(52) U.S. Cl.
CPC .......... *A61B 8/4494* (2013.01); *A61B 8/0883* (2013.01); *A61B 8/54* (2013.01); *B06B 1/0622* (2013.01)

(58) Field of Classification Search
CPC . B06B 1/0622; A61B 8/4494; A61B 8/08883; A61B 8/54
See application file for complete search history.

(56) References Cited

U.S. PATENT DOCUMENTS

| | | | | |
|---|---|---|---|---|
| 3,768,306 | A * | 10/1973 | Stearns | G01N 29/265 73/625 |
| 4,880,010 | A * | 11/1989 | Szilard | B06B 1/0622 600/457 |
| 2010/0275692 | A1* | 11/2010 | Meyer | B06B 1/0629 73/627 |
| 2012/0144920 | A1* | 6/2012 | Wong | G01S 15/8915 73/632 |
| 2016/0058425 | A1* | 3/2016 | Wong | A61B 8/06 600/453 |
| 2018/0199917 | A1* | 7/2018 | Zheng | G01S 7/52079 |

* cited by examiner

*Primary Examiner* — J. San Martin
(74) *Attorney, Agent, or Firm* — ScienBiziP, P.C.

(57) ABSTRACT

An ultrasonic sensing device includes an ultrasonic signal transmitting element and an ultrasonic signal receiving element. The ultrasonic signal transmitting element is configured to produce ultrasonic waves. The ultrasonic signal receiving element is configured to receive ultrasonic waves. The ultrasonic signal transmitting element and the ultrasonic signal receiving element are positioned at a same plane. A distance between the ultrasonic signal transmitting element and the ultrasonic signal receiving element is adjustable. The ultrasonic signal transmitting element is capable of emitting ultrasonic waves having a conical shape.

12 Claims, 3 Drawing Sheets

ULTRASONIC SENSING DEVICE

FIELD

The subject matter herein generally relates to sensors, and particularly to an ultrasonic sensing device.

BACKGROUND

Ultrasonic sensors have many advantages such as small size, low cost, safety, and widespread use as medical devices. The ultrasonic sensors can be used for medical diagnosis. However, results obtained from the ultrasonic sensors may not be accurate. Therefore, there is room for improvement in the art.

BRIEF DESCRIPTION OF THE DRAWINGS

Implementations of the present technology will now be described, by way of example only, with reference to the attached figures.

DETAILED DESCRIPTION

Figure 1:
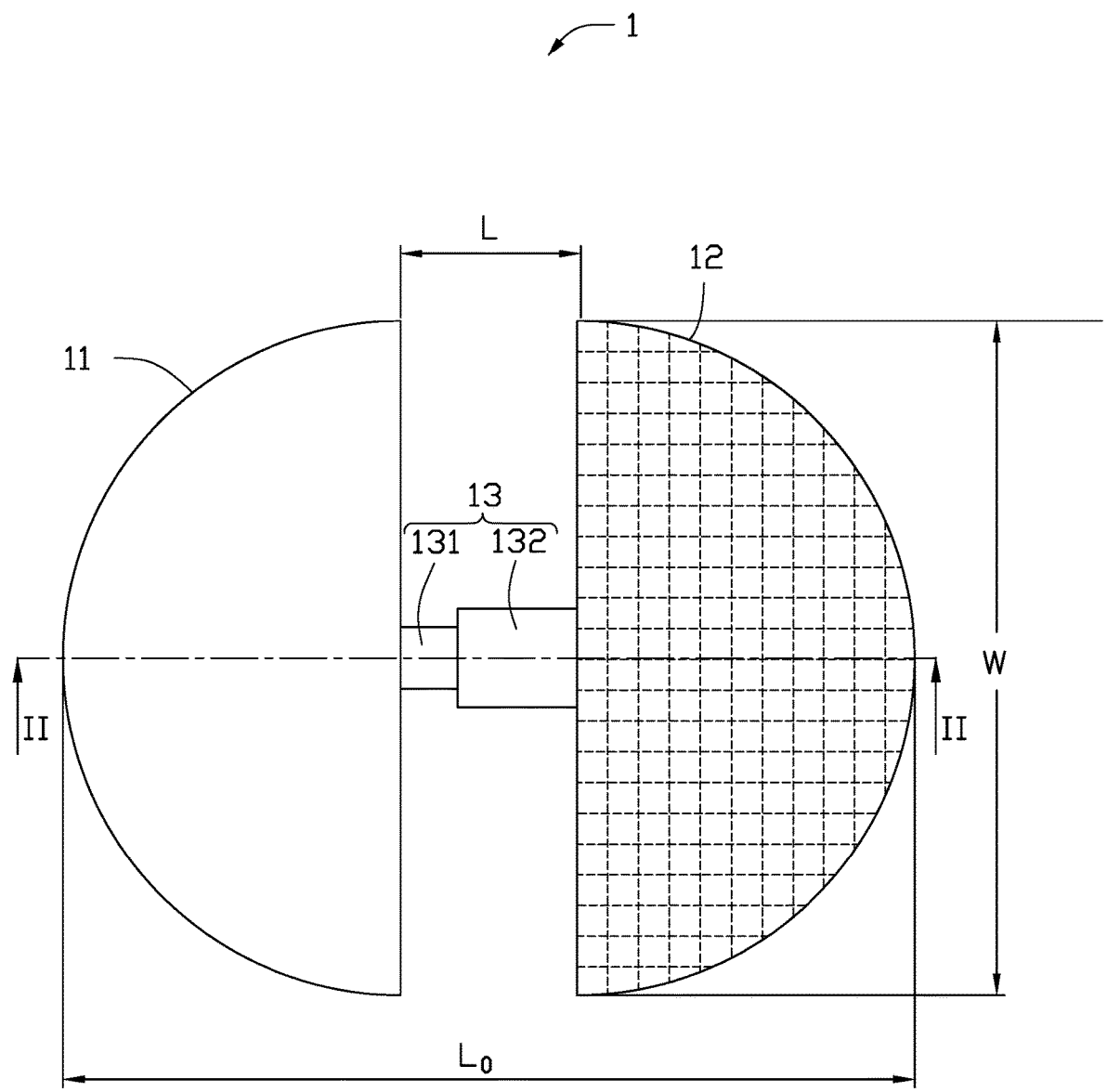
FIG. 1 is planar view of an exemplary embodiment of an ultrasonic sensing device.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein may be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

The term "coupled" is defined as connected, whether directly or indirectly through intervening components, and is not necessarily limited to physical connections. The connection can be such that the objects are permanently connected or releasably connected. The term "comprising" when utilized, means "including, but not necessarily limited to"; it specifically indicates open-ended inclusion or membership in the so-described combination, group, series, and the like.

FIG. 1 illustrates an ultrasonic sensing device 1 according to an exemplary embodiment. The ultrasonic sensing device 1 includes an ultrasonic signal transmitting element 11 and an ultrasonic signal receiving element 12. The ultrasonic signal transmitting element 11 and the ultrasonic signal receiving element 12 are coplanar and spaced apart from each other.

In the present exemplary embodiment, both the ultrasonic signal transmitting element 11 and the ultrasonic signal receiving element 12 are substantially semicircular. The ultrasonic sensing device 1 has a maximum length $L_0$ of about 58.5 mm, a width W of about 35 mm, and a thickness T (shown in FIG. 2) of about 3 mm.

A distance L between the ultrasonic signal transmitting element 11 and the ultrasonic signal receiving element 12 is adjustable. In the present exemplary embodiment, the distance L is from about 0 to about 5 mm. When the distance L is zero, the ultrasonic signal transmitting element 11 is in direct contact with the ultrasonic signal receiving element 12. When the ultrasonic signal transmitting element 11 and the ultrasonic signal receiving element 12 are spaced from each other by the largest distance L, the ultrasonic sensing device 1 has the maximum length $L_0$.

A distance regulator 13 is coupled between the ultrasonic signal transmitting element 11 and the ultrasonic signal receiving element 12. The distance regulator 13 is configured to adjust the distance L. In the present exemplary embodiment, the distance regulator 13 includes a sliding bar 131 coupled to the ultrasonic signal transmitting element 11 and a guiding sleeve 132 coupled to the ultrasonic signal receiving element 12. The sliding bar 131 is slideably received in the guiding sleeve 132. The distance L may be adjusted by sliding the sliding bar 131 along the guiding sleeve 132.

In other embodiments, the distance L may be adjusted by other elements or by other manner, not limited to the distance regulator 13.

Figure 2:
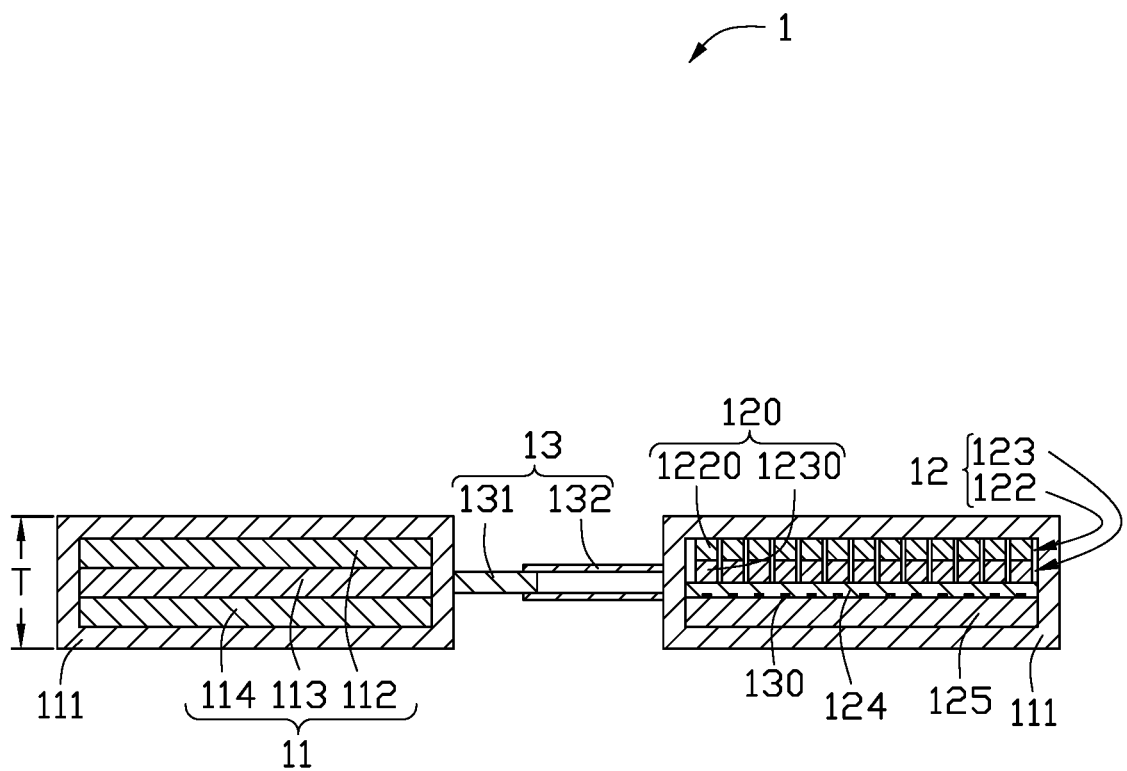
FIG. 2 is a cross-sectional view of the ultrasonic sensing device along line II-II of FIG. 1.

As shown in FIG. 2, the ultrasonic signal transmitting element 11 includes a second electrode layer 114, a first piezoelectric material layer 113 stacked on the second electrode layer 114, and a first electrode layer 112 stacked on the first piezoelectric material layer 113. The first piezoelectric material layer 113 is positioned between the first electrode layer 112 and the second electrode layer 114. The first electrode layer 112 and the second electrode layer 114 cooperatively form an electrical field, and the first piezoelectric material layer 113 vibrates and produces ultrasonic wave under the electrical field. The ultrasonic signal transmitting element 11 is wrapped by a protecting layer 111 to protect the ultrasonic signal transmitting element 11.

As shown in FIG. 2, the ultrasonic signal receiving element 12 includes a second piezoelectric material layer 123 and a third electrode layer 122 stacked on the second piezoelectric material layer 123. A circuit board 125 is stacked at the bottom of the second piezoelectric material layer 123. A binder layer 124 is positioned between the signal receiving layer 123 and the circuit board 125, binding the signal receiving layer 123 and the circuit board 125 together. The ultrasonic signal receiving element 12 is wrapped by another protecting layer 111 to protect ultrasonic signal receiving element 12.

As shown in FIG. 2, the third electrode layer 122 is a discontinuous layer and includes a plurality of electrode units 1220 spaced apart from each other. The second piezoelectric material layer 123 is a discontinuous layer and includes a plurality of piezoelectric material units 1230 spaced apart from each other. Each of the plurality of electrode units 1220 is stacked on one piezoelectric material unit 1230. Each piezoelectric material unit 1230 and one electrode unit 1220 cooperatively form an ultrasonic signal receiving unit 120. Thus, the ultrasonic signal receiving element 12 includes a plurality of discrete ultrasonic signal receiving units 120. Each of the plurality of discrete ultrasonic signal receiving units 120 includes a piezoelectric material unit 1230 and an electrode unit 1220 stacked on the piezoelectric material unit 1230. Each of the plurality of discrete ultrasonic signal receiving units 120 is capable of receiving ultrasonic signals independently and producing electric charges independently.

The circuit board 125 includes a controlling circuit (not shown) and the controlling circuit includes a plurality of sensing electrodes 130. That is, the plurality of sensing electrodes 130 is a portion of the controlling circuit. Each of the plurality of sensing electrodes 130 electrically couples one of the piezoelectric material units 1230 to the controlling circuit, and is configured to collect the electric charges and input the electric charges to the controlling circuit. The controlling circuit may be configured to convert the electric charges into electrical signals.

In the present exemplary embodiment, the circuit board 125 is a thin film transistor array substrate. In other embodiments, the circuit board 125 may be a flexible printed circuit board.

In order to make the sensing electrodes 130 effectively collect the electric charges representing readings from the sensors, the binder layer 124 has a square resistance of less than 150 Ω/sq cm, and a dielectric constant of less than 5 F/m. In addition, the binder layer 124 has a high resistance along a horizontal direction. In the present exemplary embodiment, the binder layer 124 is an anisotropic conductive film.

Both the first piezoelectric material layer 113 and the second piezoelectric material layer 123 are made of a piezoelectric material, such as polyvinylidene fluoride or lead zirconate titanate piezoelectric ceramic. In one exemplary embodiment, the first piezoelectric material layer 113 is made of lead zirconate titanate piezoelectric ceramic. Lead zirconate titanate piezoelectric ceramic is capable of producing ultrasonic waves having high intensities. The second piezoelectric material layer 123 is made of polyvinylidene fluoride, as polyvinylidene fluoride has a good ability of absorbing ultrasonic waves and can provide ultrasonic wave signals having high intensities.

The first electrode layer 112, the second electrode layer 114, and the third electrode layer 122 are made of an electrically-conductive material, such as silver, copper, molybdenum, or indium tin oxide.

Figure 3:
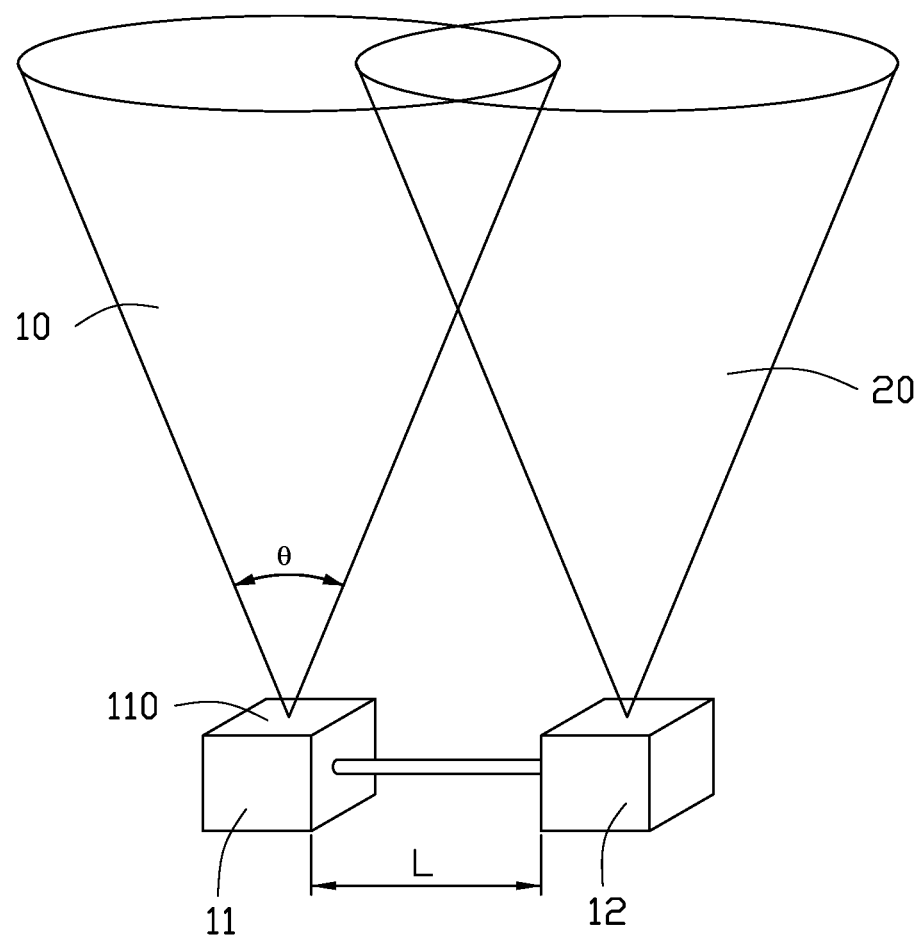
FIG. 3 is a schematic diagram demonstrating a working principle of the ultrasonic sensing device of FIG. 1.

As shown in FIG. 3, the ultrasonic signal transmitting element 11 is capable of emitting ultrasonic waves 10 having a conical shape. The ultrasonic signal transmitting element 11 includes an emitting surface 110 to emit the ultrasonic waves 10. A center axis of the ultrasonic waves 10 having the conical shape is perpendicular to the plane of the emitting surface 110. A cone angle θ of the ultrasonic waves 10 having the conical shape is adjustable. In the present exemplary embodiment, the cone angle θ of the ultrasonic waves 10 can be adjusted from about 0 to about 45 degrees. When the ultrasonic waves 10 is reflected back by an object (not shown), the reflected ultrasonic waves 20 would be received by the ultrasonic signal receiving element 12. It is experimentally found that when the distance L is adjusted from about 0 to 5 mm, and the cone angle of the ultrasonic waves 10 is controlled from about 0 to about 45 degrees, a maximum of the reflected ultrasonic waves 20 can be received by the ultrasonic signal receiving element 12.

In use, the ultrasonic sensing device 1 is held against skin of a human body at a position corresponding to a target area to be investigated. For example, the object to be investigated is a heart of a human being. An electric field (not shown) is formed between the first electrode layer 112 and the second electrode layer 114, and the first piezoelectric material layer 113 vibrates and produces ultrasonic waves under the electric field. The ultrasonic waves pass through the skin and subcutaneous fatty tissue and reach the heart. The heart reflects the ultrasonic waves back to the ultrasonic signal receiving element 12, and the ultrasonic signal receiving element 12 receives the reflected ultrasonic signals and converts the reflected ultrasonic signals to electrical signals. The reflected ultrasonic waves are received by the second piezoelectric material layer 123, and the second piezoelectric material layer 123 produces sensed charges. The sensed charges are collected by the plurality of sensing electrodes 130 and input to the controlling circuit and then output.

It is to be understood, even though information and advantages of the present exemplary embodiments have been set forth in the foregoing description, together with details of the structures and functions of the present exemplary embodiments, the disclosure is illustrative only. Changes may be made in detail, especially in matters of shape, size, and arrangement of parts within the principles of the present exemplary embodiments to the full extent indicated by the plain meaning of the terms in which the appended claims are expressed.

What is claimed is:

1. An ultrasonic sensing device comprising:
an ultrasonic signal transmitting element, the ultrasonic signal transmitting element configured to produce ultrasonic waves;
an ultrasonic signal receiving element, the ultrasonic signal receiving element configured to receive ultrasonic waves produced by the ultrasonic signal transmitting element and reflected back by an object on the ultrasonic sensing device;
wherein the ultrasonic signal transmitting element and the ultrasonic signal receiving element are coplanar; a distance between the ultrasonic signal transmitting element and the ultrasonic signal receiving element is adjustable from 0 to about 5 mm; the ultrasonic signal transmitting element is capable of emitting ultrasonic waves having a conical shape.

2. The ultrasonic sensing device of claim 1, wherein a cone angle of the conically shaped ultrasonic waves is adjustable from 0 to about 45 degrees.

3. The ultrasonic sensing device of claim 1, wherein the ultrasonic signal transmitting element comprises an emitting surface to emit the ultrasonic waves; a center axis of the conically-shaped ultrasonic waves being perpendicular to the plane of the emitting surface.

4. The ultrasonic sensing device of claim 1, wherein the ultrasonic signal transmitting element comprises a first electrode layer, a second electrode layer, and a first piezoelectric material layer between the first electrode layer and the second electrode layer.

5. The ultrasonic sensing device of claim 4, wherein the ultrasonic signal receiving element comprises a second piezoelectric material layer and a third electrode layer, stacked on the second piezoelectric material layer.

6. The ultrasonic sensing device of claim 5, wherein a circuit board is stacked at a side of the second piezoelectric material layer away from the third electrode layer; the second piezoelectric material layer is electrically coupled to the circuit board by a binder layer.

7. The ultrasonic sensing device of claim 6, wherein the circuit board comprises a plurality of sensing electrodes configured to collect sensing charges and input the sensing charges to the controlling circuit.

8. The ultrasonic sensing device of claim 6, wherein the circuit board is a thin film transistor substrate or a flexible printed circuit board.

9. The ultrasonic sensing device of claim 6, wherein the binder layer has a square resistance of less than 150 Ω/sq cm.

10. The ultrasonic sensing device of claim 6, wherein the binder layer is an anisotropic conductive film.

11. The ultrasonic sensing device of claim 5, wherein the third electrode layer comprises a plurality of electrode units spaced apart from each other; the second piezoelectric material layer comprises a plurality of piezoelectric material units spaced apart from each other; each of the plurality of electrode units is stacked on one of the plurality of piezoelectric material units; each of the plurality of piezoelectric material units and one corresponding electrode unit cooperatively form an ultrasonic signal receiving unit.

12. The ultrasonic sensing device of claim 1, further comprising a distance regulator, wherein the distance regulator is coupled between the ultrasonic signal transmitting element and the ultrasonic signal receiving element; the distance regulator is configured to adjust the distance between the ultrasonic signal transmitting element and the ultrasonic signal receiving element.

\* \* \* \* \*